United States Patent [19]

Shaw et al.

[11] Patent Number: 4,848,337

[45] Date of Patent: Jul. 18, 1989

[54] ABHERENT SURGICAL INSTRUMENT AND METHOD

[76] Inventors: Robert F. Shaw, 1560 Willow Rd., Palo Alto, Calif. 94304; Philip E. Eggers, 855 Clayton Dr., Worthington, Ohio 43085

[21] Appl. No.: 874,814

[22] Filed: Jun. 13, 1986

Related U.S. Application Data

[63] Continuation of Ser. No. 641,937, Aug. 20, 1984, abandoned, which is a continuation of Ser. No. 548,358, Nov. 3, 1983, abandoned, which is a continuation of Ser. No. 271,452, Jun. 8, 1981, abandoned, which is a continuation-in-part of Ser. No. 73,927, Sep. 10, 1979, abandoned.

[51] Int. Cl.⁴ .............................................. A61B 17/38
[52] U.S. Cl. ................................... 128/303.1; 30/140
[58] Field of Search ........... 128/303.1, 303.13, 303.14, 128/303.17, 303.11, 303.12, 399, 24.1; 30/140; 219/221, 227, 229, 230, 233, 235–240, 243; 228/51–55; 156/583

[56] References Cited

U.S. PATENT DOCUMENTS

| | | | |
|---|---|---|---|
| 2,923,640 | 2/1960 | Buckingham | 128/DIG. 14 X |
| 3,786,814 | 1/1974 | Armao | 128/303.1 |
| 3,889,680 | 6/1975 | Armao | 128/303.1 |
| 4,022,215 | 5/1977 | Benson | 128/303.1 |
| 4,074,718 | 2/1978 | Morrison, Jr. | 128/303.14 |
| 4,161,950 | 7/1979 | Doss et al. | 128/303.14 |
| 4,202,336 | 5/1980 | VanGerven | 128/303.1 |
| 4,219,025 | 8/1980 | Johnson | 128/303.1 |

FOREIGN PATENT DOCUMENTS

| | | |
|---|---|---|
| 2315075 | 3/1973 | Fed. Rep. of Germany . |
| 2621553 | 11/1977 | Fed. Rep. of Germany . |
| 1427415 | 9/1973 | United Kingdom . |
| 2002236 | 7/1978 | United Kingdom . |
| 1534472 | 12/1978 | United Kingdom . |

OTHER PUBLICATIONS

Kirk–Othmer Encyclopedia of Chemical Technology, vol. 1 at pp. 1–9 (3rd Ed. 1978).
Encyclopedia of Polymer Science and Technology, vol. 1 at p. 1 (1964).

*Primary Examiner*—Michael H. Thaler

[57] ABSTRACT

Method and means are disclosed for preventing tissue from adhering to surgical apparatus while operating at tissue temperatures at which hemostasis with minimal tissue damage occurs, and include interposing between the surgical apparatus and the tissue being heated thereby an abherent coating which exhibits electrical insulation and thermal impedance, thickness and thermal drop thereacross within specified limits.

17 Claims, 4 Drawing Sheets

ABHERENT SURGICAL INSTRUMENT AND METHOD

CROSS REFERENCE TO RELATED APPLICATIONS

This is a continuation of application Ser. No. 641,937 filed Aug. 20, 1984, abandoned which is a continuation of application Ser. No. 548,358 filed Nov. 3, 1983, abandoned, which is a continuation of application Ser No. 271,452, filed June 8, 1981, abandoned, which is a continuation-in-part of application Ser. No 073,927 filed Sept. 10, 1979, abandoned, all entitled "Abstract Surgical Instrument and Method" and filed by Robert Francis Shaw and Philip E. Eggers.

BACKGROUND OF THE INVENTION

Surgical devices which heat the tissue to provide hemostasis are described in the literature (see, for example, U.S. Pat. Nos. Re. 29,088, 4,091,813, and 4,185,632). The adherence of tissue to such surgical devices severely limits their usefulness because the resulting avulsion of tissue causes undesirable tissue damage and bleeding. Also, the adherence of tissue to such surgical devices limits the surgeon's control of the device, and the build-up of adherent tissue material causes apparent dullness of the device. Additionally, the build-up of adherent tissue material on electrical heater-type surgical devices introduces a high thermal impedance between the heater and the tissue being cut that prevents heating of the tissues to the desired temperature. These problems of tissue adhering to the surgical device are especially severe for tissue temperatures within the range from about 100° C. to about 500° C.

SUMMARY OF THE INVENTION

Applicant has discovered that the tissue temperature for the optimum condition of hemostasis with minimal tissue damage varies with the type of tissue being cut and may be as low as about 130° C. (on the soft palate of the mouth) and as high as about 450° C. to 500° C. (on highly vascularized tissue), above which tissue adherence usually does not occur. In accordance with the present invention, the optimum conditions of hemostasis with minimal tissue damage can be attained by operating at tissue temperatures in the range from about 100° C. to about 500° C. and by introducing between the surgical device and the contacted tissue an abherent coating having specific thermal parameters.

More particularly, in surgical apparatus which includes an electrical heater operating at elevated temperatures for heating the tissue contacted thereby, the heat transfer from the apparatus to the tissue in regions of the apparatus in contact with tissues may be twenty times greater than the heat transfer from the apparatus to the air in regions of the apparatus that are not in contact with tissue. The heat transfer conditions vary widely as a function of the type of tissue being cut, the desired operating temperature, and the speed at which the device is moved through tissue.

To obtain optimum conditions of hemostasis with minimal tissue damage, the surgical device should rapidly elevate the temperature of the tissue to a preselected narrow range (usually between 100° C. and 500° C.) and should maintain the tissue temperature within that range as cutting proceeds.

Any accumulation of tissue on that portion of the surgical device that contacts tissue can interpose a thermal impedance between the device and the tissues which may inhibit heat transfer and cause the temperature of the contacted tissue to drop below the value at which the optimum conditions of hemostasis with minimal tissue damage occur. Therefore, according to the present invention, an abherent coating is provided on the tissue-contacting surface of the surgical device which has thermal properties and characteristics within specific limits to assure that the temperature of tissue remains within the optimum range for which hemostasis and minimal tissue damage occur. In addition, the abherent coating according to the present invention electrically insulates the electrical heater from the tissue being cut and also electrically insulates the separate sections of the electrical heater from being shorted by the contacted tissue.

DETAILED DESCRIPTION OF THE PREFERRED EMBODIMENTS

Figure 1:
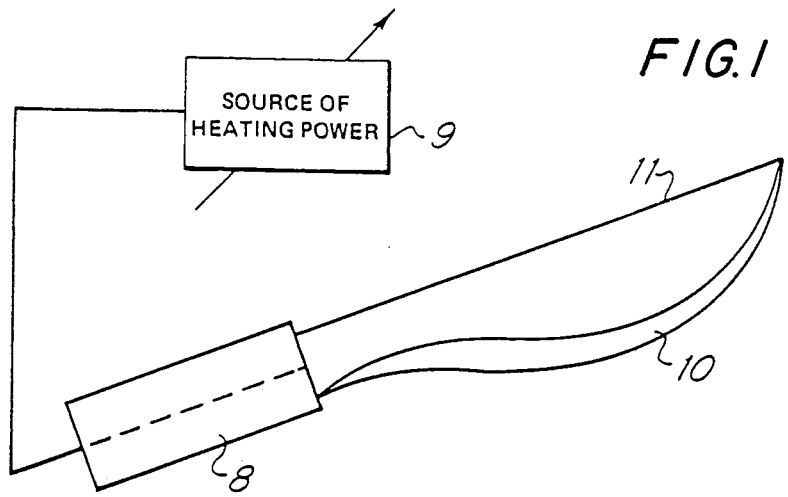
FIG. 1 is a pictorial representation of an electrically-heated scalpel.
Figure 2:
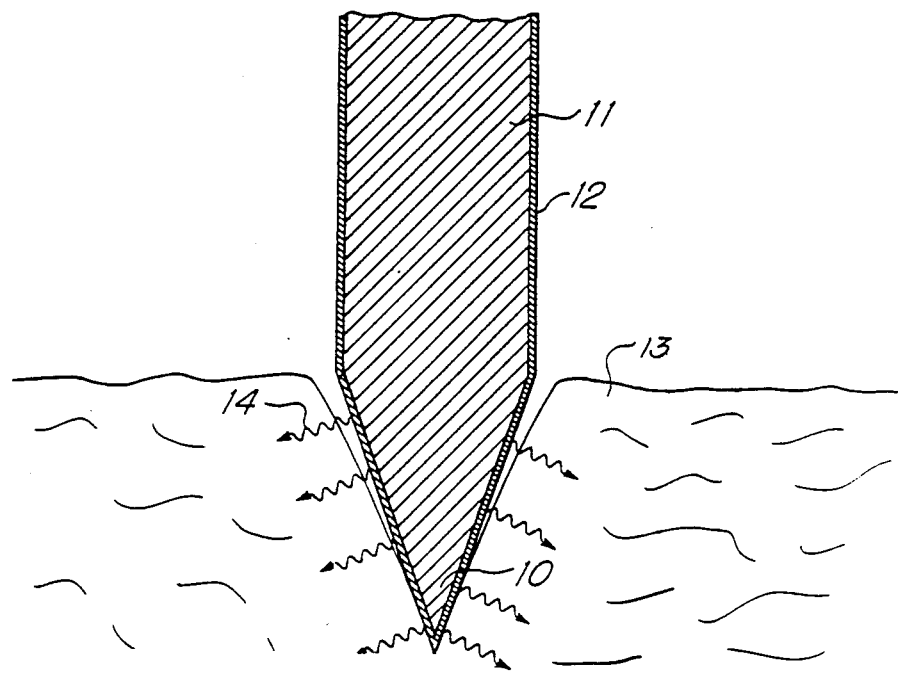
FIG. 2 is a cross-sectional view of one embodiment of the present invention in which a heated surgical scalpel includes an abherent coating.
Figure 1A:
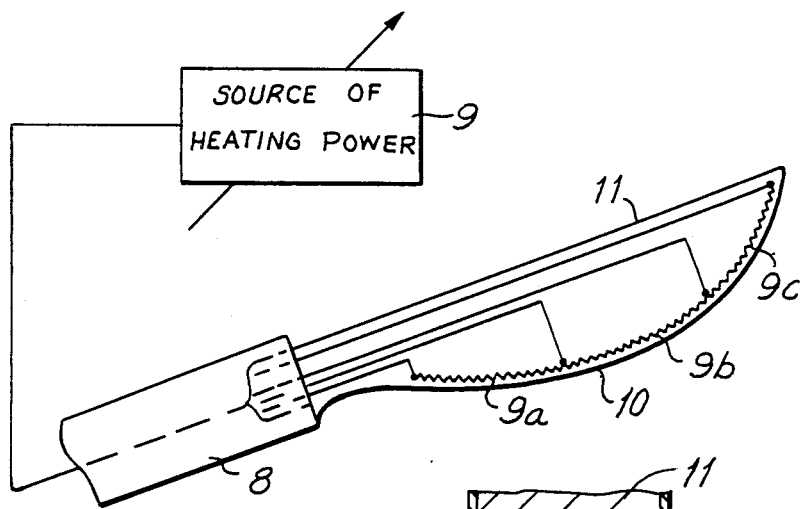
FIG. 1a is a pictorial representation of a scalpel according to FIG. 1 having electrical heater segments disposed along the tissue-cutting edge.
Figure 2A:
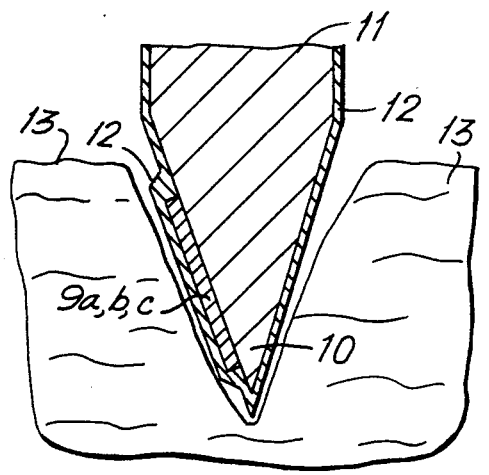
FIG. 2a is a cross-sectional view of the scalpel of the embodiment of FIG. 1a including an abherent coating.

Referring now to FIG. 1, there is shown a surgical scalpel having a blade portion 11 with a cutting edge 10 and an attached handle portion 8 which also carries a conductor of heating power from source 9 to the blade 11 to heat the same, as taught in the prior art. In particular, such prior art schemes for heating the blade 11, as disclosed in U.S. Pat. Nos. 3,768,482 and 3,826,263, include a plurality of heater segments 9a, b and c disposed near and along the tissue-cutting edge 10 to dissipate power from source 9 under independent electrical controls in response to the cooling thereof from contact with the tissue 13 being cut. As shown in FIG. 1a and in the cross-sectional view of FIG. 2a, these electrical heater segments 9a, b and c are positioned near the cutting edge 10 of the blade to assure close thermal contact with the tissue 13. The surfaces of the blade 11, at least near the cutting edge 10, therefore operate at elevated temperatures and contact tissue 13 via an abherent coating 12 interposed between the blade 11, the electrical heater segments 9a, b and c, and the tissue 13. This eliminates the problem of tissue 13 sticking to the surfaces of blade 11 or the heater segments 9a, b and c but introduces a thermal impedance therebetween.

It has been determined that for portions of the blade 11 in contact with tissue, the heat flux 14 normal to or through the abherent coating 12 is approximately 10 to 20 times greater than the heat flux therethrough to the air for portions of the blade 11 not in contact with tissue. This produces temperature differences across the abherent coating 12. Thus, while the blade 11 is out of contact with tissue 13, the effective surface temperature of abherent coating 12 is approximately the same as the temperature of the blade 11. However, when the blade 11 and abherent coating 12 contact the tissue 13, the heat flux 14 passing through the thermal impedance presented by abherent coating 12 causes the surface temperature of abherent coating 12 to decrease below the desired temperature at which the optimum condition of hemostasis and minimal tissue damage occur. The temperature of the surface of abherent coating 12 may be increased to the desired temperature by increasing the temperature of the blade 11 by an amount sufficient to overcome the thermal drop across the abherent coating 12. However, because of the transient conditions associated with the blade 11 being in and out of contact with tissue 13 during a surgical procedure, the surface temperature of the abherent coating 12 may rise excessively while out of contact with tissue to cause deterioration of the abherent coating 12 and undesirable tissue damage upon recontact with tissue 13, as well as falling excessively when coming into contact with tissues to temperatures that are not hemostatic.

In contrast to these transient operating conditions in surgery, conventional cookware with abherent coatings do not involve transient operation. The heat transfer rate to an item being cooked is generally constant and is established without regard for damage to living tissue. Cookware also can be operated at higher temperatures to overcome the effects of high thermal impedance associated with thicker abherent coatings. However, for reasons stated above, surgical devices cannot be arbitrarily set at a temperature significantly higher than the optimum temperature at which hemostasis with minimal tissue damage occurs. Also, the thicknesses of coatings typically used on cookware cannot be used on surgical devices because of the blunting effect and degradation of the cutting action of a blade that would result.

In accordance with the present invention, the abherent coating 12 may be formed as a solid layer or as a sacrificial solid layer or as a sacrificial liquid layer. A solid abherent layer 12 may be formed on the blade 11 and heater segments 9a, b and c including materials such as fluorocarbon polymers (exemplified by the fluorinated ethylenepropylene copolymers, polytetrafluoroethylene and polyethylene terephthalate) which also electrically insulate the heater segments 9a, b, and c from the tissue being cut and from each other so that contacted tissue cannot short adjacent heater segments. In other embodiments, the abherent layer 12 may include such materials as silicones and polydimethylsiloxanes with active end groups, for example, of hydroxyl, amine, epoxide or thiol attached to the silicone polymer via a nonhydrolyzable Si-C bond, or fluoride-metal composites such as fluoride impregnated composites, or organic phosphates. Alternatively, a sacrificial solid abherent coating may be formed using materials such as silicone greases or hydrocarbon, synthetic and natural ester waves, or sulfide compounds. In addition, a sacrificial solid abherent coating may be formed using fluorinated ethylenepropylene copolymers which have been found to be effective in that a coating thus formed "sloughs off" in thin platelets with use to provide the desired abherent characteristics with respect to tissue.

Figure 4:
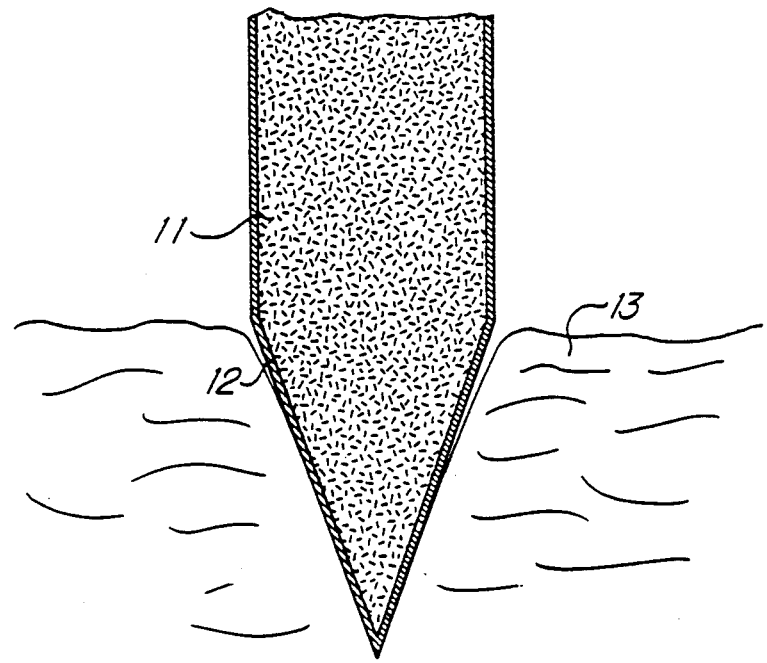
FIG. 4 is a cross-sectional view of another embodiment of the present invention in which a sintered porous blade structure with interconnecting passages provides a reservoir of abherent material.

With respect to FIG. 4, a sacrificial liquid abherent coating may be provided by forming a sintered or porous blade structure 11 with substantially continuous passages therethrough which can be impregnated with a material such as silicone oil, for example, of the type based on dimethyl silicone, or ethers such as perfluoropolysynthetic fluids. The porous and impregnated structure according to FIG. 4 thus establishes and maintains a continuous film of abherent material 12 at the surface of the device 11 which is disposed to contact tissue 13.

Figure 5:
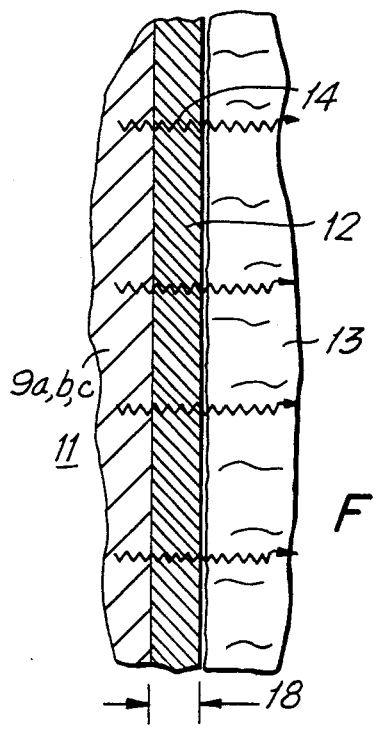
FIG. 5 is a detailed cross-sectional view of an embodiment of the present invention which illustrates the abherent coating on the surgical instrument disposed adjacent to the tissue being cut.

In accordance with the present invention, the thermal impedance of the abherent coating must be sufficiently low to permit transfer of heat 14, as illustrated in FIG. 5, from the hot surface which may be heater segments 9a, b and c or blade 11 to the tissue 13 in contact therewith. In particular, the tolerable thermal impedance of an abherent coating 12 depends generally upon the level of heat flux required for a particular surgical application. For example, in ophthalmic, neurological and plastic, and dermatological surgery procedures, hemostasis can be accomplished while cutting using heat fluxes well below 50 watts/cm$^2$. However, surgical procedures involving incisions in highly vascular tissues or rapid movement through tissue may require heat fluxes above 50 watts/cm$^2$ to achieve hemostasis while cutting.

As used herein, "thermal impedance" is defined as follows:

$$R = \frac{\Delta T}{(Q/A)}$$

where
R refers to the thermal impedance of the abherent coating in units of $$\frac{°C \cdot cm^2}{watt}.$$

ΔT refers to the temperature difference across the abherent coating from the interface of the device 11/abherent coating 12 to the outer surface of the abherent coating 12, in units of °C.

Q/A refers to the heat flux flowing normal to or through the abherent coating, in units of watts/cm$^2$.

Referring to FIG. 5, the maximum allowed temperature difference ΔT across the abherent coating under maximum heat flux conditions should not substantially exceed about 50° C. in order to optimize hemostasis while minimizing tissue damage and avoiding exposure of the surgical device and the abherent coating to damaging temperatures. This tolerable temperature difference thus establishes the thermal impedance for the heat flux levels that will be encountered during use of the surgical device. The thermal impedances, as defined above, for abherent coatings 12 operating at specified levels of heat flux are summarized below:

| Heat Flux, Q/A (watts/cm$^2$) | Maximum Allowed Thermal Impedance, R, for Temperature Difference, ΔT, of 50° C. |
|---|---|
| 10 | 5.0 |

| Heat Flux, Q/A (watts/cm²) | Maximum Allowed Thermal Impedance, R, for Temperature Difference, ΔT, of 50° C. |
| --- | --- |
| 20 | 2.5 |
| 30 | 1.7 |
| 40 | 1.3 |
| 50 | 1.0 |
| 100 | 0.5 |

These values of thermal impedance for the abherent coating can establish the maximum allowed thickness 18 for various abherent coatings. Referring to FIG. 5, the allowed thickness of abherent coating 12 in a direction normal to the heat flux 14 is given by the relationship:

$$t = R \cdot k$$

where t refers to the maximum allowed abherent coating thickness in units of centimeters, R is the thermal impedance, as defined previously, and k refers to effective thermal conductivity of abherent coating 12 in units of watts/cm°C.

Figure 6:
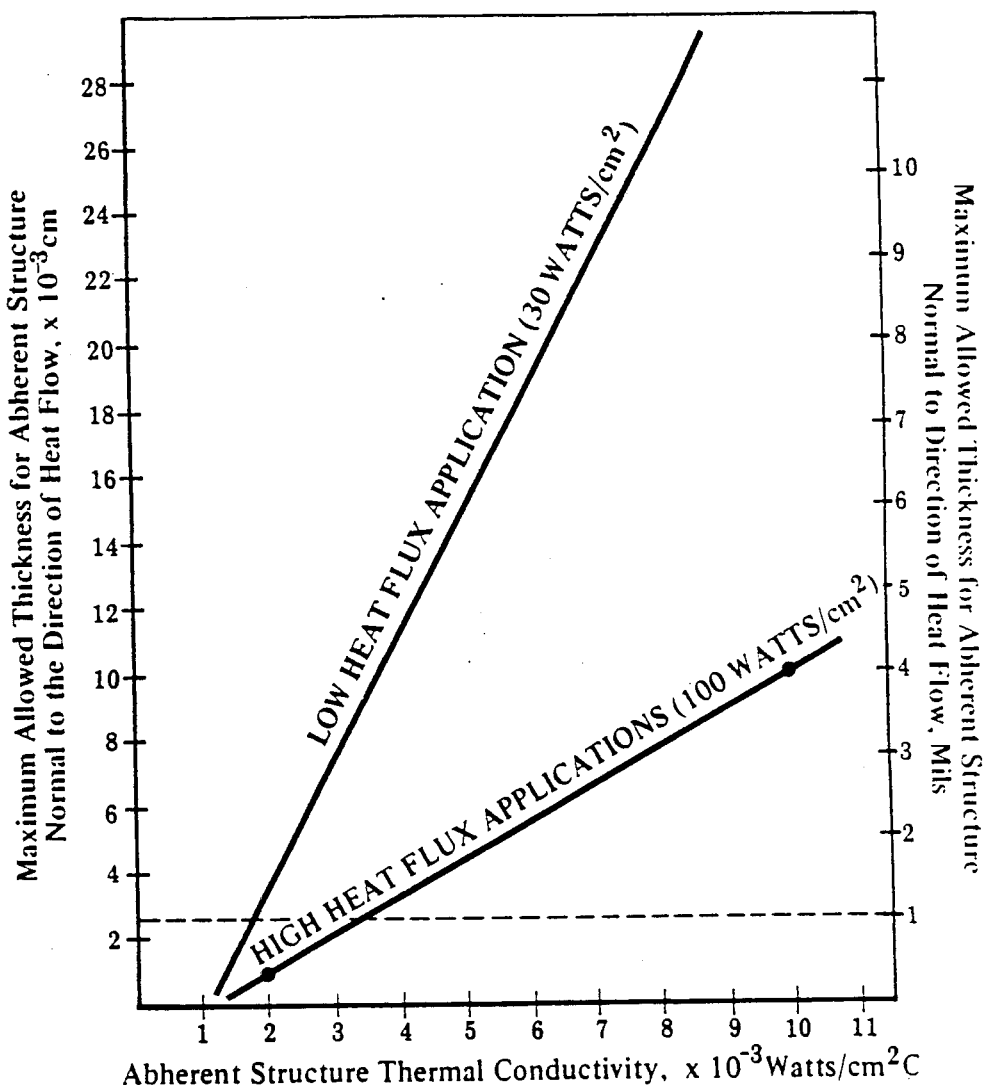
FIG. 6 is a graph which illustrates the parameters of an abherent coating according to the present invention.

The graph of FIG. 6 illustrates the relationship between maximum thickness 18 of the abherent coating 12 and heat flux levels corresponding to high (100 watts/cm² maximum) and low (30 watts/cm² maximum) heat flux requirements associated with various surgical procedures. By way of example, certain fluorocarbon materials that have been found effective as abherent coatings exhibit negligible electrical conductivity and a thermal conductivity of about 0.0025 watts/cm°C. In accordance with the above, the thickness of an abherent coating of this material should not be greater than 0.0013 cm (0.5 mil) for operation at high heat flux levels. Such as abherent coating nevertheless provides adequate electrical isolation between the electrical signals in the heater segments and the tissue being cut.

Figure 3:
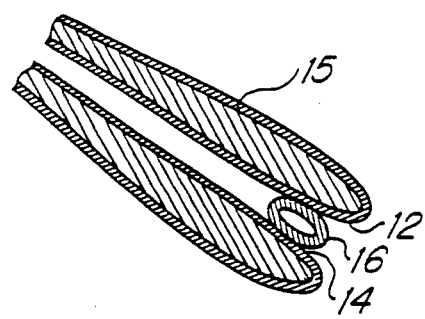
FIG. 3 is a cross-sectional view of another embodiment of the present invention in which a heated surgical hemostat includes an abherent coating.

In the apparatus of FIG. 3, a pinch-type instrument 15 (such as a hemostat) may be heated in conventional manner by a source of heating power connected thereto to transfer heat 14 to tissue 16 via the abherent coating 12 interposed therebetween. The maximum allowed thickness of abherent coating 12 is determined, as discussed above, with respect to the thermal impedance of the coating material and the operating level of heat flux involved.

We claim:

1. A surgical apparatus for hemostatic cutting of tissue under surgical conditions comprising a scalpel blade, means for heating the blade to a preselected temperature in the range from about 100° C. to about 500° C. for causing hemostasis of cut tissue with minimal tissue damage, the means for heating selectively delivering heat to those areas of the blade selectively cooled by heat transfer from the blade to the tissue thereby maintaining the blade substantially at the preselected temperature, and an electrically insulating abherent coating on the scalpel blade for contactng the tissue to be cut, thermally conducting heat flux from the blade to the tissue, and reducing the accumulation of cut tissue on the apparatus so that the tissue to be cut may be cut and heated with a temperature drop across the abherent coating not substantially exceeding about 50° C., the coating having an inner side in thermal contact with the blade or means for heating and an outer side for contacting tissue.

2. The apparatus of claim 1 wherein the abherent coating has a thermal impedence of less than 5° C.-cm²/watt.

3. The apparatus of claim 1 wherein the abherent coating comprising a material selected from the group consisting of silicones, polydimethylsiloxanes, fluoride-metal composites and fluorocarbon polymers.

4. The apparatus of claim 1 wherein the abherent coating comprises a porous or scintered material having substantially continuous passageways therethrough and being impregnated with an abherent sacrificial material for reducing the accumulation of cut tissue on the apparatus.

5. The apparatus of claim 4 wherein the abherent sacrificial material is selected from the group consisting of silicone oils and ethers.

6. The apparatus of claim 1 wherein the thickness of the abherent coating is not greater than 0.5 mil.

7. The apparatus of claim 1 wherein the abherent coating is a solid.

8. A method for hemostatic cutting of tissue with minimal tissue damage under surgical conditions comprising:

providing a surgical apparatus comprising a scalpel blade having coated thereon an electrically insulating abherent coating;

heating the blade to a preselected substantially constant temperature in the range from about 100° C. to about 500° C., the temperature being selected for producing in the type of tissue being cut substantial hemostasis with minimal tissue damage;

cutting the tissue with the heated coated blade so that heat is transferred from the blade through the abherent coating to the tissue being cut;

selectively heating those areas of the blade that are cooled by transfer of heat from the blade to the tissue as the tissue is cut in order to maintain the scalpel substantially at the preselected temperature; and providing the abherent coating with a thermal impedence so that the temperature drop across the abherent coating does not substantially exceed about 50° C.

9. The method of claim 8 wherein the thermal impedence of the abherent coating is less than 5° C.-cm²/watt.

10. The method of claim 8 wherein the abherent coating comprises a sacrificial abherent material that is exuded from the surgical apparatus.

11. The method of claim 10 wherein the sacrificial abherent material is selected from the group consisting of silicone oils and ethers.

12. The method of claim 8 wherein the thickness of the abherent coating is not greater than 0.5 mil.

13. The method of claim 8 wherein the abherent coating is a solid.

14. A surgical apparatus for causing hemostasis of tissue under surgical conditions comprising a scalpel blade, means for heating the scalpel blade to a preselected temperature in the range from about 100° C. to about 500° C. for causing hemostasis of tissue with minimal tissue damage, the means for heating selectively delivering heat to those areas of the scalpel blade selectively cooled by heat transfer from the scalpel blade to the tissue to maintain the scalpel blade substantially at the preselected temperature, wherein the surgical apparatus further comprises:

an electrically insulating abherent coating for contacting the tissue, thermally conducting heat flux from the scalpel blade to the tissue, and reducing the accumulation of tissue on the apparatus whereby the temperature drop across the abherent coating does not substantially exceed about 50° C., the coating having an inner side in thermal contact with the scalpel blade or means for heating and an outer side for contacting tissue.

15. The apparatus of claim 14 wherein the abherent coating has a thermal impedence of less than 5° C.-$cm^2$/watt.

16. The apparatus of claim 15 wherein the thickness of the abherent coating is not greater than 0.5 mil.

17. The apparatus of claim 16 wherein the abherent coating is a solid.

* * * * *